(12) United States Patent
Schönholz et al.

(10) Patent No.: US 7,029,488 B2
(45) Date of Patent: Apr. 18, 2006

(54) MECHANICAL THROMBECTOMY DEVICE FOR USE IN CEREBRAL VESSELS

(75) Inventors: Claudio Javier Schönholz, Shreveport, LA (US); Gerald Dorros, Scottsdale, AZ (US); Michael Hogendijk, Palo Alto, CA (US)

(73) Assignee: Gore Enterprise Holdings, Inc., Newark, DE (US)

( * ) Notice: Subject to any disclaimer, the term of this patent is extended or adjusted under 35 U.S.C. 154(b) by 0 days.

(21) Appl. No.: 10/278,183

(22) Filed: Oct. 21, 2002

(65) Prior Publication Data

US 2003/0158518 A1    Aug. 21, 2003

Related U.S. Application Data

(63) Continuation-in-part of application No. 09/972,225, filed on Oct. 4, 2001.

(60) Provisional application No. 60/314,269, filed on Aug. 22, 2001.

(51) Int. Cl.
*A61M 29/00* (2006.01)

(52) U.S. Cl. .................................................. 606/200

(58) Field of Classification Search ............ 604/46.01, 604/523, 528, 530–533, 538, 101.04, 104–109; 606/200, 191, 944, 198
See application file for complete search history.

(56) References Cited

U.S. PATENT DOCUMENTS

| | | | | | |
|---|---|---|---|---|---|
| 5,041,093 | A | * | 8/1991 | Chu | 604/104 |
| 5,876,367 | A | * | 3/1999 | Kaganov et al. | 604/8 |
| 5,911,734 | A | * | 6/1999 | Tsugita et al. | 606/200 |
| 6,168,579 | B1 | * | 1/2001 | Tsugita | 604/96.01 |
| 6,280,413 | B1 | * | 8/2001 | Clark et al. | 604/104 |
| 6,336,934 | B1 | * | 1/2002 | Gilson et al. | 606/200 |
| 6,361,546 | B1 | * | 3/2002 | Khosravi | 606/200 |
| 6,468,291 | B1 | * | 10/2002 | Bates et al. | 606/200 |
| 6,544,280 | B1 | * | 4/2003 | Daniel et al. | 606/200 |
| 6,569,150 | B1 | * | 5/2003 | Teague et al. | 604/524 |
| 6,656,202 | B1 | * | 12/2003 | Papp et al. | 606/200 |
| 6,656,351 | B1 | * | 12/2003 | Boyle | 210/136 |
| 6,685,722 | B1 | * | 2/2004 | Rosenbluth et al. | 606/200 |
| 6,702,834 | B1 | * | 3/2004 | Boylan et al. | 606/200 |
| 2004/0049225 | A1 | * | 3/2004 | Denison | 606/200 |

* cited by examiner

*Primary Examiner*—Cris Rodriguez
(74) *Attorney, Agent, or Firm*—Kevin J. Boland

(57) ABSTRACT

Apparatus and methods for treating cerebral occlusions are provided, including a thrombectomy device having at least one deployable element. The deployable element is advanced through the occlusion in a contracted state, then self-deploys distal of the occlusion or, alternatively, may be deployed to a wide range of configurations using a physician-actuated deployment knob. The thrombectomy device then may be retracted to cause the deployable element to snare the occlusion, and/or rotated circumferentially to cause the fibrin strands of the occlusion to be wrapped around the deployable element.

15 Claims, 6 Drawing Sheets

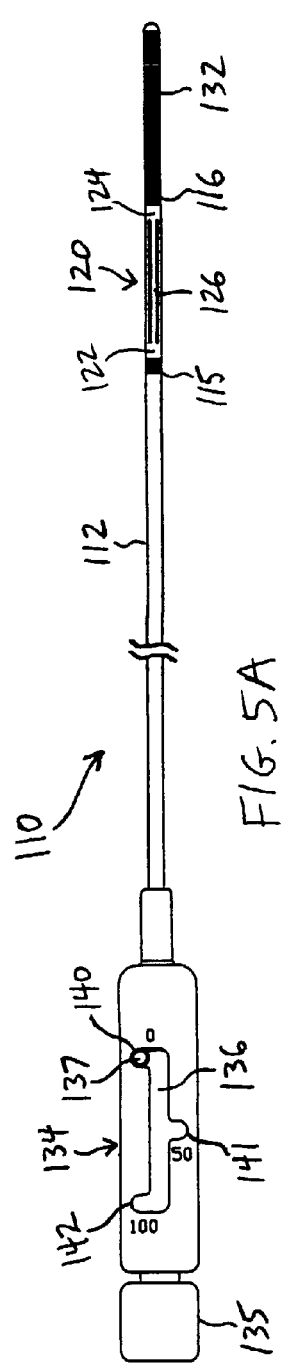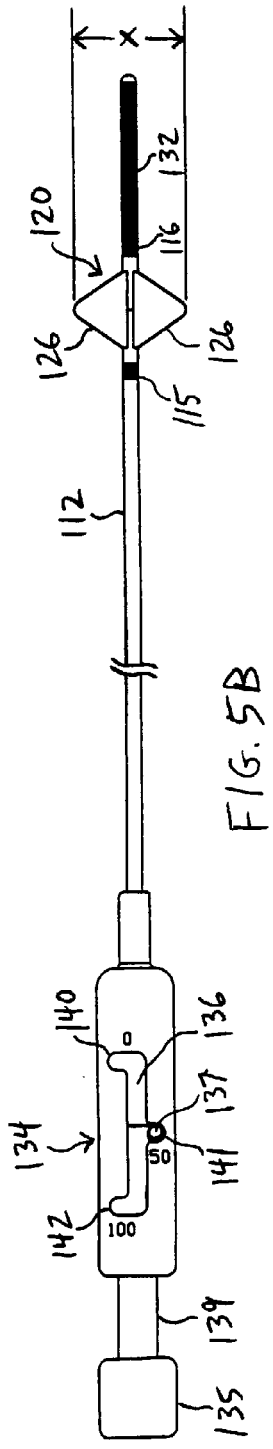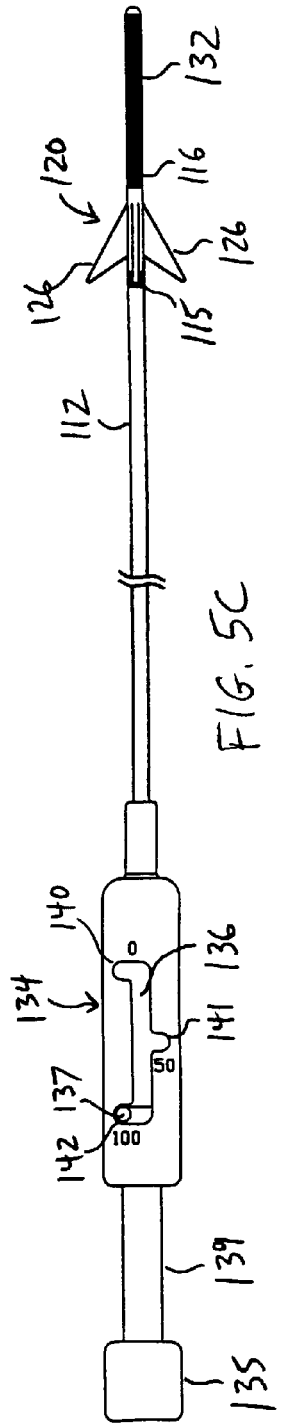

US 7,029,488 B2

MECHANICAL THROMBECTOMY DEVICE FOR USE IN CEREBRAL VESSELS

REFERENCE TO RELATED APPLICATION

The present application is a continuation-in-part of U.S. patent application Ser. No. 09/972,225, filed Oct. 4, 2001.

FIELD OF THE INVENTION

The present invention relates to improved apparatus and methods for removal of vascular occlusions. More specifically, the apparatus and methods of the present invention are directed to removing cerebral occlusions by providing a device having at least one deployable element configured to snare and/or rotationally engage fibrin strands of the occlusion.

BACKGROUND OF THE INVENTION

Cerebral occlusions that lead to stroke require swift and effective therapy to reduce morbidity and mortality rates associated with the disease. Many current technologies for treating stroke are inadequate because emboli generated during the procedure may travel downstream from the original occlusion and cause ischemia. There is currently a need for a stroke treatment system that provides a swift and efficient treatment for occlusions while simultaneously controlling cerebral flow characteristics.

In the initial stages of stroke, a CT scan or MRI may be used to diagnose the cerebral occlusion, which commonly occurs in the middle cerebral arteries. Many current technologies position a catheter proximal of the occlusion, then deliver clot dissolving drugs to treat the lesion. A drawback associated with such technology is that delivering drugs may require a period of up to six hours to adequately treat the occlusion. Another drawback associated with lytic agents (i.e., clot dissolving agents) is that they often facilitate bleeding.

When removing a thrombus using mechanical thrombectomy devices, it is beneficial to engage the thrombus and remove it as cleanly as possible, to reduce the amount of emboli that are liberated. However, in the event that emboli are generated during mechanical disruption of the thrombus, it is imperative that they be subsequently removed from the vasculature.

Several methods are known for mechanically removing clots to treat cerebral occlusions. For example, U.S. Pat. No. 5,895,398 to Wensel et al. (Wensel) describes a shape-memory coil affixed to an insertion mandrel. The coil is contracted to a reduced profile state within the lumen of a delivery catheter, and the catheter is used to cross a clot. Once the coil is disposed distal of the clot, the coil is deployed and retracted proximally to engage and remove the clot.

A primary drawback associated with the device described in the Wensel patent is that the deployed coil contacts the intima of the vessel, and may damage the vessel wall when the coil is retracted to snare the occlusion. Additionally, the configuration of the coil is such that the device may not be easily retrieved once it has been deployed. For example, once the catheter has been withdrawn and the coil deployed distal of the occlusion, it may be difficult or impossible to exchange the coil for another of different dimensions.

U.S. Pat. No. 5,972,019 to Engelson et al. (Engelson) describes a deployable cage assembly that may be deployed distal of a clot. Like the Wensel device, the device described in the Engelson patent is depicted as contacting the intima of the vessel, and presents the same risks as the Wensel device. In addition, because the distal end of the device comprises a relatively large profile, the risk of dislodging emboli while crossing the clot is enhanced, and maneuverability of the distal end of the device through tortuous vasculature may be reduced.

In view of these drawbacks of previously known devices, it would be desirable to provide apparatus and methods for removal and recovery of thrombi and/or emboli above the carotid bifurcation.

It also would be desirable to provide apparatus and methods that quickly and efficiently treat cerebral occlusions while reducing trauma imposed upon cerebral vessels.

It further would be desirable to provide apparatus and methods for a thrombectomy device that may be used to snare an occlusion and/or rotationally engage fibrin strands of the occlusion.

It still further would be desirable to provide apparatus and methods for a thrombectomy device that selectively may be actuated to deploy to a plurality of deployment configurations while disposed within a treatment vessel.

SUMMARY OF THE INVENTION

In view of the foregoing, it is an object of the present invention to provide apparatus and methods for removal and recovery of thrombi and/or emboli above the carotid bifurcation.

It also is an object of the present invention to provide apparatus and methods that quickly and efficiently treat cerebral occlusions while reducing trauma imposed upon cerebral vessels.

It further is an object of the present invention to provide apparatus and methods for a thrombectomy device that may be used to snare an occlusion and/or rotationally engage fibrin strands of the occlusion.

It is a further object of the present invention to provide apparatus and methods for a thrombectomy device that selectively may be actuated to deploy to a plurality of deployment configurations while disposed within a treatment vessel.

These and other objects of the present invention are accomplished by providing a thrombectomy device having proximal and distal ends and an occlusion engagement section disposed near the distal end. The engagement section comprises proximal and distal ends and at least one deployable element disposed therebetween. The deployable element has a contracted state suitable for insertion into a vessel and at least one deployed state in which the deployable element extends radially outward from the engagement section. In one of the deployed states, the deployable element preferably comprises a hook shape configured to snare an occlusion when the thrombectomy device is retracted proximally. The deployable element further is configured to engage and wrap fibrin strands of the occlusion about the deployable element when the thrombectomy device is rotated circumferentially.

In a first embodiment of the present invention, the thrombectomy device comprises a catheter body affixed to the proximal end of the engagement section, an atraumatic tip affixed to the distal end of the engagement section, and a handle disposed at the proximal end of the thrombectomy device.

In a preferred method of operation, an emboli removal catheter is advanced over a guidewire and disposed proximal of an occlusion. Natural or suction-assisted aspiration is provided through the emboli removal catheter to induce a retrograde flow in the treatment vessel. With retrograde flow established, the guidewire is advanced through the occlusion. A micro catheter having a lumen then is advanced over the guidewire and through the occlusion, and the guidewire is removed from within the micro catheter.

The engagement section of the thrombectomy device is advanced distally through the lumen of the micro catheter with the deployable element being constrained in the contracted state within the micro catheter. Once the deployable element is advanced distal of the micro catheter, the deployable element self-deploys to the predetermined, preferably hook shape.

At this time, the thrombectomy device may be retracted proximally to cause the deployable element to snare the occlusion, and/or rotated circumferentially to cause the deployable element to engage and wrap fibrin strands of the occlusion about the deployable element. Emboli generated during the procedure are directed into the emboli removal catheter due to the established retrograde flow in the treatment vessel. An increased level of retrograde flow temporarily may be provided through the emboli removal catheter to enhance retrograde flow during disruption of the occlusion. Upon satisfactory removal of thrombi and/or emboli, the deployable element is retracted proximally and contracted against the distal end of the emboli removal catheter, then removed from the patient's vessel.

In an alternative embodiment of the present invention, the above-described thrombectomy device comprises a physician-actuated handle used to deploy the deployable element to a plurality of configurations. In this embodiment, a rod affixed to a deployment knob engages selected notches of the handle that represent the various deployment configurations.

When the rod engages a first notch, the deployable element is provided in a contracted state. When the deployment knob is actuated by a physician and the rod engages a second notch, the deployable element is transformed to a fully deployed state. At least one intermediate notch also may be provided to allow the deployable element to be deployed to at least one intermediate state between the contracted and fully deployed states.

The thrombectomy device of the alternative embodiment preferably is used in conjunction with the above-described emboli removal catheter. In operation, the distal end of the thrombectomy device, which has handling characteristics similar to those of a traditional guidewire, is advanced through the emboli removal catheter and through the occlusion under retrograde flow conditions. When the deployable element is disposed distal of the occlusion, e.g., under fluoroscopic guidance, a physician actuates the deployment knob to transform the deployable element from the contracted state to either the fully deployed state or an intermediate state. The thrombectomy device then is retracted proximally to cause the deployable element to snare the occlusion, and/or rotated circumferentially to wrap the fibrin strands of the occlusion about the deployable element, as described hereinabove. Upon removal of thrombi and/or emboli, the deployment knob is actuated to return the deployable element to the contracted state for removal.

BRIEF DESCRIPTION OF THE DRAWINGS

Further features of the invention, its nature and various advantages will be more apparent from the accompanying drawings and the following detailed description of the preferred embodiments, in which:

FIGS. 5A–5C are, respectively, top views illustrating an alternative thrombectomy device of the present invention in contracted, intermediate and fully deployed states;

DETAILED DESCRIPTION OF THE INVENTION

Figure 1A:
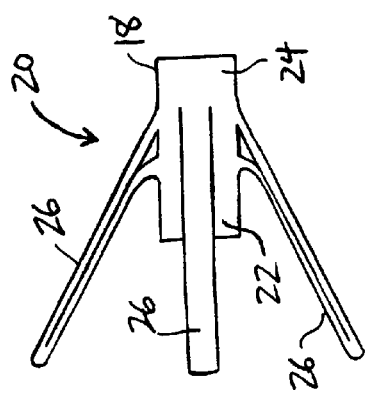
FIGS. 1A–1B provide side views illustrating features of a deployable element of the present invention.
Figure 1B:
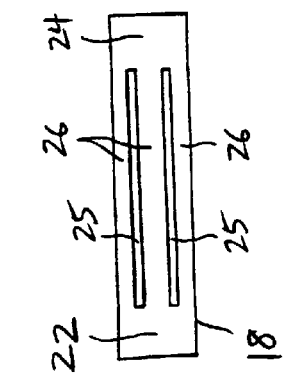

Referring to FIG. 1, a preferred method for manufacturing a hook-shaped deployable element, for use with a thrombectomy device of the present invention, is described. In FIG. 1A, tubular member 18 having proximal and distal ends 22 and 24 and a lumen extending therebetween is provided and preferably comprises a shape memory material, for example, a nickel-titanium alloy (commonly known in the art as Nitinol). Plurality of longitudinal slits 25 are formed at selected locations about the circumference of tubular member 18 to define at least one deployable element 26. As shown in FIG. 1A, plurality of longitudinal slits 25 preferably are disposed about tubular member 18 so that they do not extend to proximal and distal ends 22 and 24 of tubular member 18.

When proximal end 22 is advanced distally with respect to distal end 24, and/or distal end 24 is advanced proximally with respect to proximal end 22, deployable element 26 becomes biased radially outward from tubular member 18. Deployable element 26 further may be biased in a proximal direction, e.g., by applying external forces, then may be heat treated to self-deploy to the predetermined hook-shaped configuration depicted in FIG. 1B. In the context of the present invention, the term "hook-shaped" refers generally to a bent shape extending radially outward from tubular member 18 and in a proximal direction.

Techniques are known for setting of a custom shape in a piece of Nitinol, e.g., by constraining the Nitinol element on a mandrel or fixture in the desired shape and applying an appropriate heat treatment. In accordance with such techniques, tubular member 18 and deployable element 26 are heat treated to form occlusion engagement section 20, which has a deployed configuration adapted to engage a cerebral occlusion, as described hereinbelow.

Figure 2:
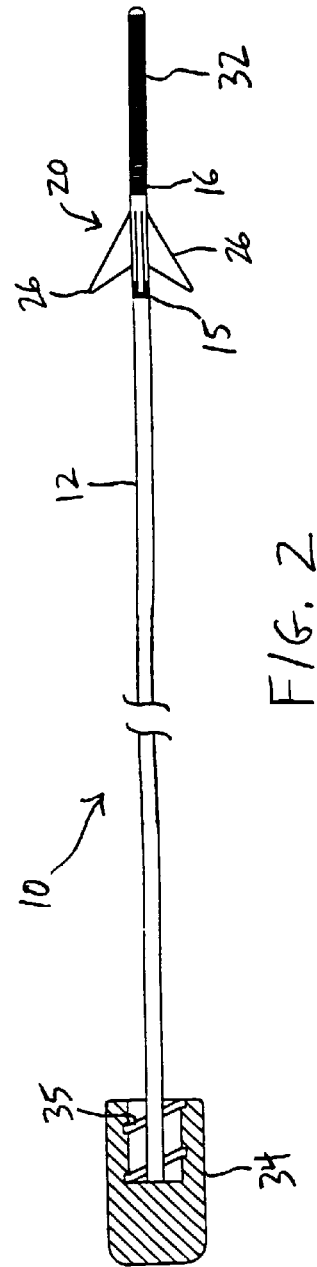
FIG. 2 provides a side view of a first embodiment of a thrombectomy device of the present invention.

Referring now to FIG. 2, thrombectomy device 10 constructed in accordance with a first embodiment of the present invention is described. Thrombectomy device 10 preferably comprises catheter body 12 having proximal and distal ends and a lumen extending therebetween, occlusion engagement section 20 of FIG. 1B, atraumatic tip 32, and handle 34, which is affixed to the proximal end of catheter body 12.

The distal end of catheter body 12 is affixed to proximal end 22 of occlusion engagement section 20, e.g., using a biocompatible adhesive, and distal end 24 of engagement section 20 is affixed to atraumatic tip 32. Atraumatic tip 32 preferably comprises a platinum coil to facilitate insertion of the distal end of device 10 under fluoroscopy. Thrombectomy device 10 preferably further comprises proximal and distal radiopaque markers 15 and 16, which may be disposed on proximal and distal ends 22 and 24 of engagement section 20, respectively. Proximal and distal radiopaque markers 15 and 16 may be used to facilitate positioning of deployable element 26 under fluoroscopy, as described hereinbelow.

Referring now to FIG. 3, thrombectomy device 10 of FIG. 2 preferably is used conjunction with a loading device and micro catheter to facilitate delivery of deployable element 26 in a contracted state to a location distal of an occlusion. In FIG. 3A, loading device 40 comprises body 41 having proximal and distal ends and bore 43 extending therebetween, and further comprises male luer fitting 42 at the proximal end and female luer fitting 44 at the distal end.

Figure 3A:
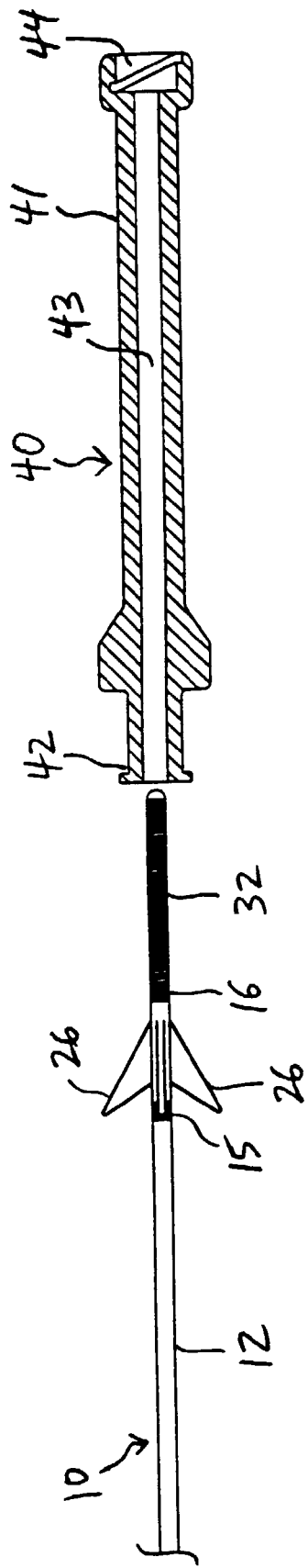
FIGS. 3A–3D are side sectional views illustrating a technique for preparing the thrombectomy device of FIG. 2 for use in a patient's vessel.
Figure 3B:
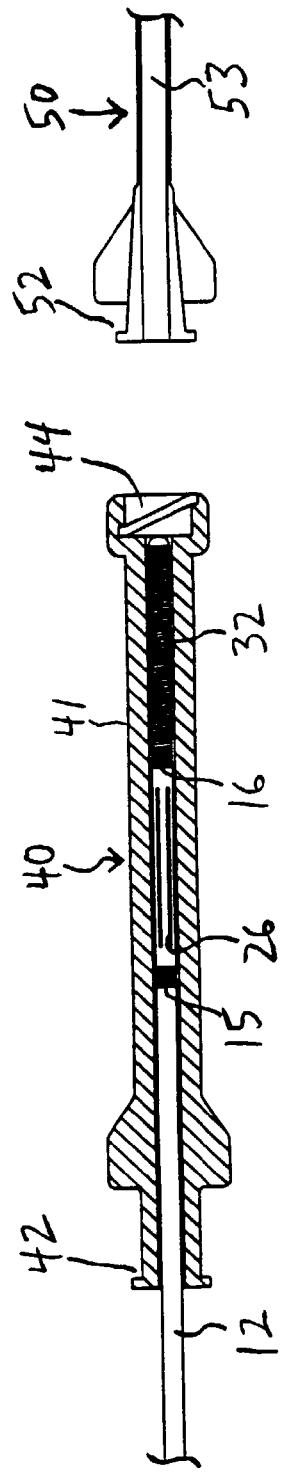

Atraumatic tip 32 and catheter body 12 comprise outer diameters that are slightly smaller than an inner diameter of bore 43. In a preferred embodiment, the outer diameters are about 0.014 inches. When deployable element 26 is provided in the contracted state, i.e., by the application of external forces, engagement section 20 comprises an outer diameter that preferably is about 0.014 inches and substantially flush with atraumatic tip 32 and catheter body 12. This allows atraumatic tip 32, engagement section 20 and the distal end of catheter body 12 to be advanced distally through bore 43, as shown in FIG. 3B. The advancement of engagement section 20 through bore 43 causes deployable element 26 to be constrained in the contracted state within bore 43.

Micro catheter 50 having proximal and distal ends and lumen 53 extending therebetween further is provided to facilitate delivery of deployable element 26. Lumen 53 preferably comprises an inner diameter that is approximately equal to the inner diameter of bore 43 of loading device 40. Micro catheter 50 further preferably comprises male luer fitting 52 at the proximal end which is configured to engage female luer fitting 44 of loading device 40.

Figure 3C:
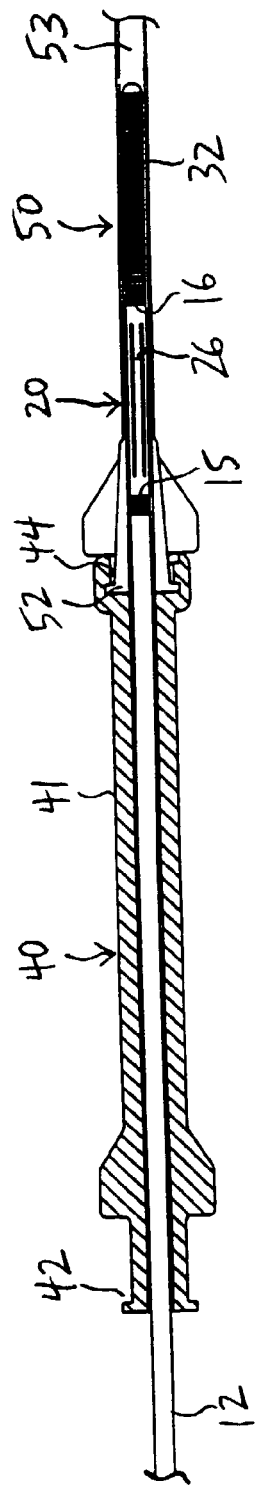

Referring now to FIG. 3C, female luer fitting 44 of loading device 40 is coupled to male luer fitting 52 of micro catheter 50 and engagement section 20 is advanced distally through lumen 53 of micro catheter 50. Deployable element 26 remains in the contracted state as engagement section 20 is advanced through micro catheter 50.

Figure 3D:
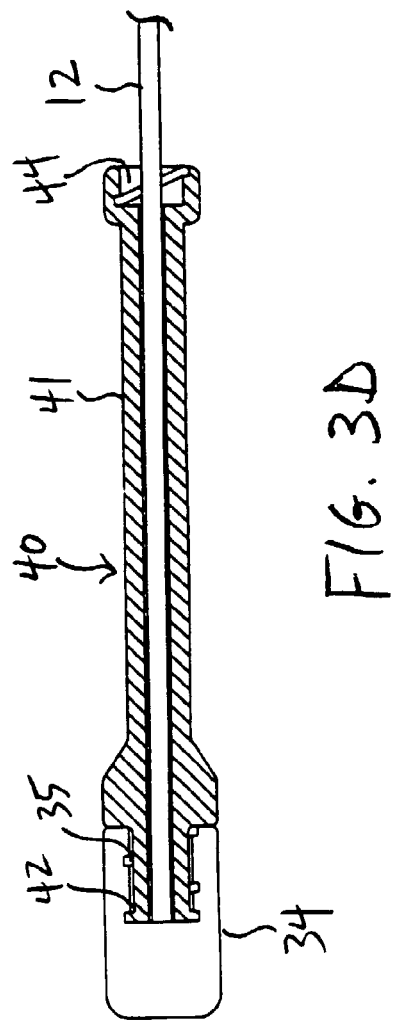

At this time, male luer fitting 52 may be disengaged from female luer fitting 44. Loading device 40 then is retracted proximally over catheter body 12 until the proximal end of loading device 40 contacts handle 34 of thrombectomy device 10. Female luer fitting 35 of handle 34 then is coupled to male luer fitting 42 of loading device 40 to provide a proximal handle assembly that is adapted to be grasped by a physician, as shown in FIG. 3D.

Referring now to FIG. 4, a preferred method for using thrombectomy device 10 to treat a cerebral occlusion is described. In a first method step, guidewire 65 is advanced through a patient's vasculature and is disposed proximal of occlusion S in treatment vessel V, e.g., a middle cerebral artery, using techniques that are per se known in the art. Emboli removal catheter 60 having proximal and distal ends, working lumen 61 extending therebetween, and occlusive element 62 disposed at the distal end is inserted over guidewire 65 with occlusive element 62 in a contracted state. The distal end of emboli removal catheter 60 is positioned at a location proximal of occlusion S, and occlusive element 62 is deployed, e.g., by inflating a balloon, to occlude antegrade flow into treatment vessel V.

A substantially continuous level of retrograde flow then is provided through working lumen 61 of emboli removal catheter 60, e.g., using natural or suction-assisted aspiration techniques described hereinbelow, to cause flow in treatment vessel V to flow in a retrograde fashion. The direction of flow in treatment vessel V is illustrated by the arrows in FIG. 4A, which is toward emboli removal catheter 60. For an occlusion S residing in a patient's cerebral vasculature, it is preferred that emboli removal catheter 60 is disposed in a patient's carotid artery.

Emboli removal catheter 60 preferably is provided in accordance with the catheter described in commonly-assigned U.S. Pat. No. 6,423,032. The proximal end of emboli removal catheter may be coupled to a venous return sheath (not shown) to form an arterial-venous shunt suitable for providing retrograde flow in treatment vessel V. This natural aspiration embodiment comprising an arterial-venous shunt is described in detail in the above-referenced patent. Alternatively, a suction-assisted aspiration device, e.g., a syringe, may be coupled to a suction port (not shown) disposed at the proximal end of emboli removal catheter 60 and may be used alone or in conjunction with the arterial-venous shunt to induce retrograde flow in treatment vessel V. With retrograde flow established in treatment vessel V using natural and/or suction-assisted techniques, guidewire 65 is advanced distally to pierce through occlusion S.

Figure 4A:
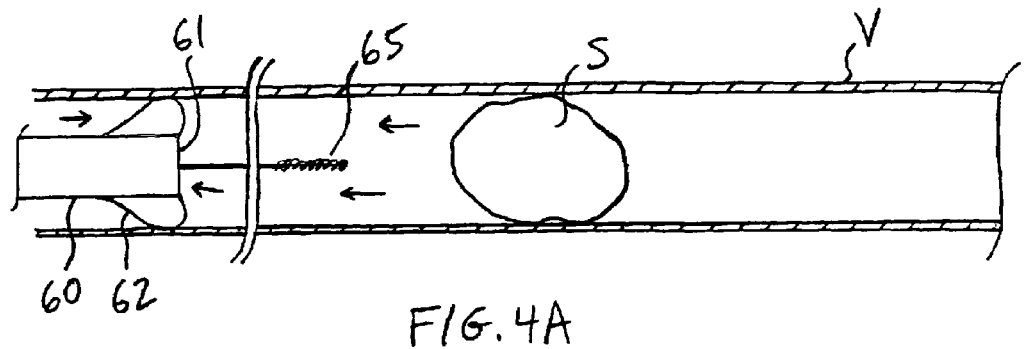
FIGS. 4A–4D are side views illustrating a preferred method of using the apparatus of FIGS. 2–3 to treat a cerebral occlusion.
Figure 4B:
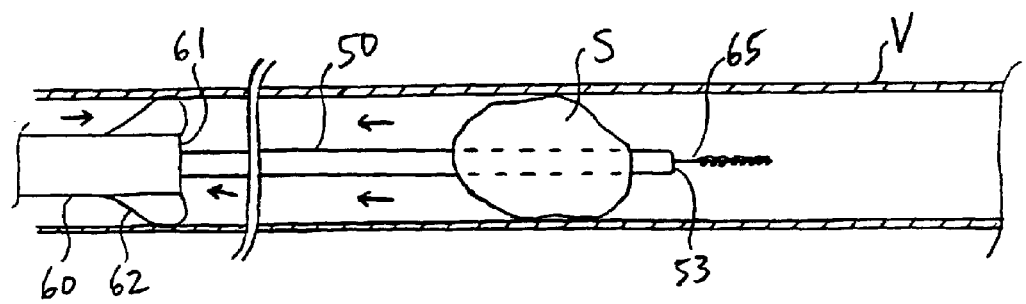

Referring now to FIG. 4B, the distal end of micro catheter 50 of FIG. 3 is advanced over guidewire 65, through working lumen 60 of emboli removal catheter 60, and through occlusion S with retrograde flow having been established in treatment vessel V. When the distal end of micro catheter 50 is disposed distal of occlusion S, guidewire 65 is retracted proximally and removed from within lumen 53 of micro catheter 50.

At this time, the steps described hereinabove with respect to FIGS. 3A–3D may be performed to facilitate insertion of deployable element 26 in the contracted state through micro catheter 50. Specifically, engagement section 20 of thrombectomy device 10 is advanced distally into loading device 40 to cause deployable element 26 to assume the contracted state. The distal end of loading device 40 then is coupled to the proximal end of micro catheter 50 and deployable element 26 is advanced distally into lumen 53 of micro catheter 50. The distal end of loading device 40 then may be disengaged from the proximal end of micro catheter 50, and the proximal end of loading device 40 then may be coupled to handle 34 and grasped by a physician.

Figure 4C:
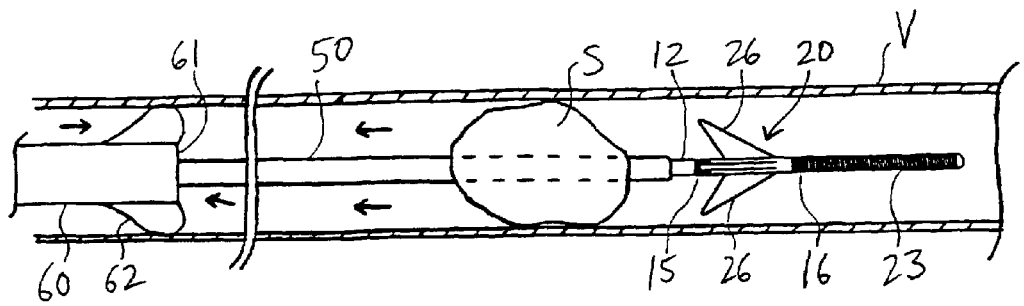

Referring now to FIG. 4C, engagement section 20 of device 10 is advanced distally through micro catheter 50 and is disposed distal of micro catheter 50 to cause deployable element 26 to self-deploy in treatment vessel V distal of occlusion S. Micro catheter 50 then may be retracted proximally through occlusion S and into the confines of emboli removal catheter 60, while deployable element 26 is held stationary distal of occlusion S.

Figure 4D:
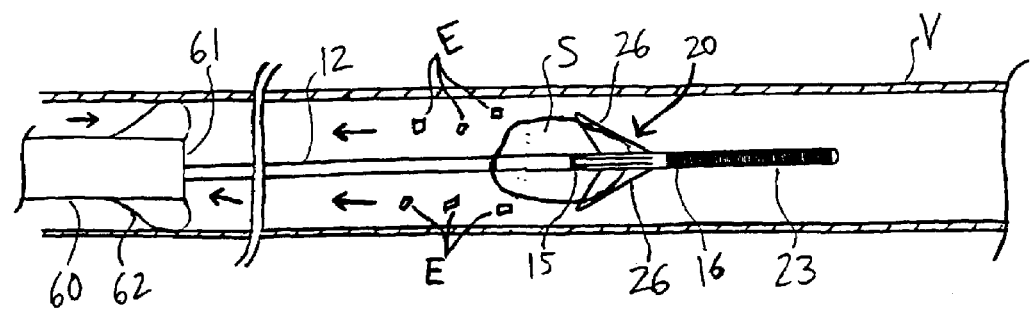

Referring now to FIG. 4D, thrombectomy device 10 of FIG. 2 may be retracted proximally to cause hook-shaped deployable element 26 to snare occlusion S, and/or rotated circumferentially to cause the fibrin strands of occlusion S to be wrapped about deployable element 26. Emboli E liberated during the procedure are directed into working lumen 61 of emboli removal catheter 60 for removal. Increased rates of suction-assisted aspiration preferably are applied, e.g., using a syringe (not shown) coupled to the proximal end of emboli removal catheter 60, when occlusion S is disrupted.

Thrombectomy device 10 then is retracted proximally under fluoroscopic guidance until deployable element 26 contacts the distal end of emboli removal catheter 60. At this time, further retraction of device 10 causes deployable element 26 to be inverted and then contracted within working lumen 61.

It should be noted that the inversion and contraction of deployable element 26 is not expected to impose significant trauma upon a patient's vasculature. This is because deployable element 26 preferably is used to remove occlusions in a patient's cerebral vasculature, e.g., a middle cerebral artery, which comprises a relatively small diameter. In the deployed state, deployable element 26 self-deploys to a predetermined outer diameter that is smaller than an inner diameter of the cerebral vessel, as depicted in FIGS. 4C–4D. Deployable element 26 then is retracted proximally through the cerebral vasculature in the deployed state under fluoroscopic guidance using radiopaque markers 15 and 16. Deployable element 26 is not inverted and contracted until it contacts the distal end of emboli removal catheter 60, which preferably is disposed in a patient's carotid artery. Because the carotid artery comprises a larger inner diameter relative to cerebral vessels, the inversion and contraction of deployable element 26 is not expected to impose significant trauma upon a patient's vasculature.

Referring now to FIG. 5, an alternative embodiment of a thrombectomy device of the present invention is described. Thrombectomy device 110 comprises occlusion engagement section 120, which preferably is provided in accordance with occlusion engagement section 20 of FIG. 1B. Specifically, engagement section 120 comprises a tubular member having a plurality of slits disposed in a lateral surface of the tubular member to form at least one deployable element 126. Deployable element 126 comprises a contracted state, as shown in FIG. 5A, and a fully deployed state, as depicted in FIG. 5C.

Preferably, deployable element 126 comprises a shape-memory material and is heat treated, using techniques described hereinabove, to be inclined to self-deploy to the fully deployed state shown in FIG. 5C. In this embodiment, deployable element 126 advantageously may be deployed to achieve a plurality of intermediate states between the contracted and fully deployed states, as illustratively shown in FIG. 5B.

Figure 6:
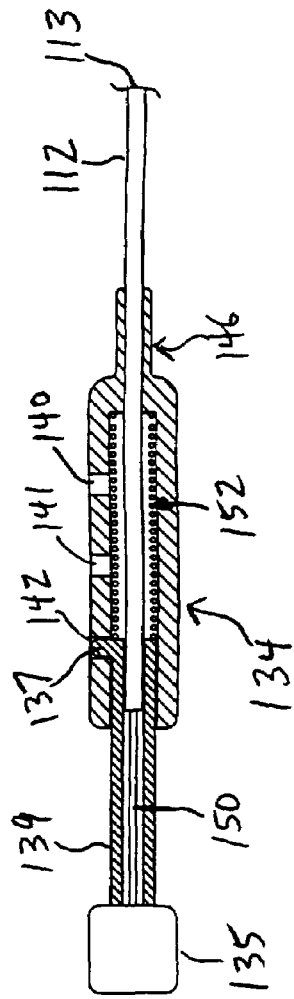
FIG. 6 provides a side sectional view of the handle of the thrombectomy device of FIGS. 5A–5C.

Thrombectomy device 110 preferably comprises catheter body 112 having proximal and distal ends and a lumen extending therebetween, handle 134, deployment knob 135, and core wire 150 having proximal and distal ends, which is disposed through the lumen of catheter body 112, as shown in FIGS. 6–7. Proximal end 122 of engagement section 120 is affixed to the distal end of catheter body 112, while distal end 124 of engagement section 126 is affixed to atraumatic tip 132.

Handle 134 preferably comprises slot 136, which is coupled to a plurality of notches. In a preferred embodiment, handle 134 comprises first notch 140 corresponding to the contracted state of deployable element 126, second notch 142 corresponding to the fully deployed state, and at least one intermediate notch 141 corresponding to an intermediate state, as described hereinbelow.

Referring now to FIG. 6, preferred features of handle 134 and deployment knob 135 are described in greater detail. Deployment knob 135 is affixed to a proximal end of rod 139. A distal end of rod 139 comprises pin 137, which is configured to be disposed in a selected notch. Rod 139 further comprises a bore extending between the proximal and distal ends that is configured to contain a proximal section of core wire 150, as shown in FIG. 6. The proximal end of core wire 150 is affixed to deployment knob 135. By advancing deployment knob 135 proximally or distally with respect to handle 134, core wire 150 translates the force to the distal end of device 110 to actuate deployable element 126, as described in detail in FIG. 7 hereinbelow.

The proximal end of catheter body 112 is disposed within handle 134, as shown in FIG. 6, and preferably is affixed to handle 134 in the vicinity of region 146. The bore of rod 139 comprises an inner diameter that is slightly larger than an outer diameter of catheter body 112 to permit rod 139 to be longitudinally advanced over catheter body 112 within handle 134. Handle 134 preferably comprises spring 152, which biases rod 139 and deployable knob 135 in a proximal direction, as shown in FIG. 6.

Referring now to FIG. 7, features of the distal end of thrombectomy device 110 are described in greater detail. Core wire 150 extends from deployment knob 135 of FIG. 6, through lumen 113 of catheter body 112, through the tubular member of engagement section 120, and preferably is affixed to distal end 124 of engagement section 120 and further affixed to atraumatic tip 132.

Figure 7A:
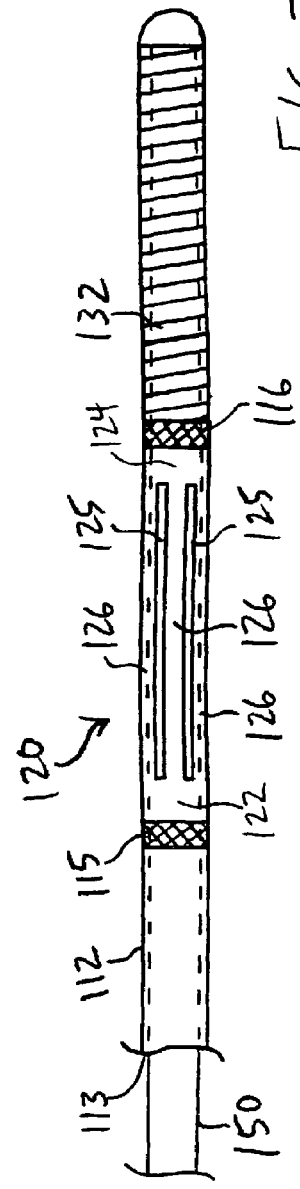
FIGS. 7A–7B are side views illustrating features of the distal end of the thrombectomy device of FIGS. 5A–5C.

In FIG. 7A, deployable element 126 is provided in a contracted state when deployment knob 135 is advanced distally and pin 137 of rod 139 is disposed within first notch 140. In the contracted state, core wire 150 serves to impose a tensile force upon engagement section 120 that prevents atraumatic tip 132 from being advanced proximally towards catheter body 112. In the contracted state, engagement section 120 preferably comprises an outer diameter of about 0.014 inches, which is substantially flush with outer diameters of atraumatic tip 132 and catheter body 112.

Figure 7B:
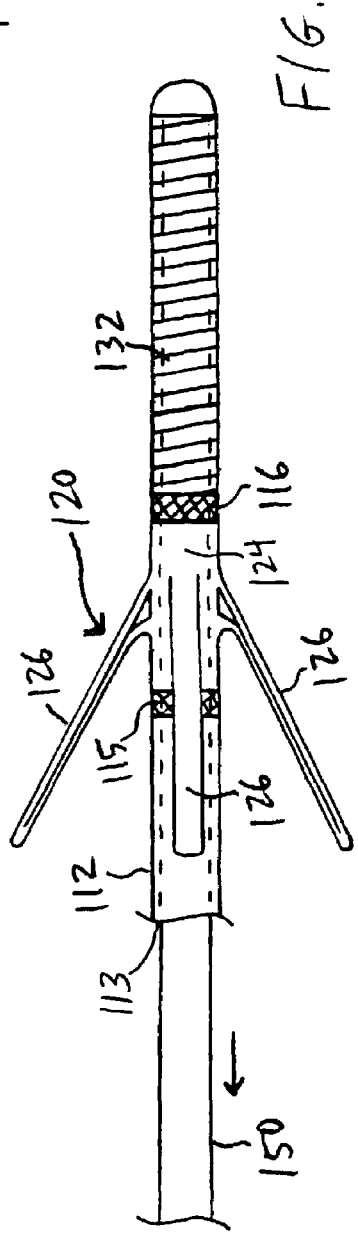

When deployment knob 135 is retracted proximally and pin 137 is disposed within second notch 142, core wire 150 also is retracted proximally to cause atraumatic tip 132 to be advanced towards catheter body 112. The retraction of core wire 150 imposes a compressive force upon engagement section 120 to cause deployable element 126 to bow radially outward and deploy to the fully deployed state, as shown in FIGS. 5C and 7B. Deployable element 126 will be inclined to assume the hook shape shown, i.e., whereby deployable element 126 extends radially outward and in a proximal direction, when heat treated to deploy to that shape using techniques described hereinabove.

Deployable element 126 also may assume any intermediate configuration between the contracted and fully deployed states by disposing pin 137 in an intermediate notch. For example, when pin 137 is disposed within intermediate notch 141, core wire 150 holds deployable element in an intermediate state, as shown in FIG. 5B. Because pin 137 is temporarily locked within notch 141, deployable element 126 will retain the intermediate configuration until pin 137 is rotated and disengaged from notch 141.

Deployable element 126 may be returned from the intermediate or fully deployed states of FIGS. 5B and 5C, respectively, to the contracted state of FIG. 5A by distally advancing deployment knob 135, which in turn causes core wire 150 to reimpose the tensile force upon engagement section 120. As will be appreciated by those skilled in the art, handle 134 may comprise any number of intermediate notches that cause deployable element 126 to deploy to any number of intermediate configurations.

The intermediate configuration depicted in FIG. 5B comprises a profile having an outer diameter 'x', which illustrates the maximum outer diameter that deployable element 126 may achieve between the contracted state shown in FIG. 5A and the fully deployed state shown in FIG. 5C. Diameter 'x' preferably is configured to be slightly smaller than an inner diameter of a treatment vessel, to reduce trauma to the treatment vessel caused by the actuation of deployable element 126.

Thrombectomy device 110 preferably comprises physical characteristics associated with those of a traditional guidewire. Specifically, core wire 150 is configured to provide pushability for the device, while atraumatic tip 132 preferably comprises a platinum coil that allows a physician to maneuver the distal end of the device through a patient's vasculature.

In operation, thrombectomy device 110 preferably is used in conjunction with emboli removal catheter 60 of FIG. 4. In a first step, emboli removal catheter 60 is advanced over a guidewire (not shown) and is disposed in a patient's vessel proximal of an occlusion. Retrograde flow then is established in treatment vessel V via working lumen 61, as described hereinabove, and the guidewire is removed from within working lumen 61.

Thrombectomy device 110 then is advanced through working lumen 61 with deployable element 126 in the contracted state shown in FIG. 5A. Atraumatic tip 132 serves to guide the distal end of thrombectomy device 110 from the distal end of emboli removal catheter 60 to the site of occlusion S in treatment vessel V. As noted hereinabove, when occlusion S is situated in a middle cerebral artery, it is preferred that emboli removal catheter 60 is disposed in a patient's carotid artery.

With retrograde flow established in treatment vessel V, atraumatic tip 132 is advanced distally to pierce through occlusion S. Thrombectomy device 110 further is advanced distally, under fluoroscopic guidance using radiopaque markers 115 and 116, until proximal radiopaque marker 115 is disposed distal of occlusion S. At this time, deployment knob 135 may be actuated, as described in detail hereinabove, to transform deployable element 126 from the contracted state to an intermediate state or the fully deployed state, as shown in FIGS. 5B-5C, respectively.

Handle 134 then may be retracted proximally to cause deployable element 126 to engage occlusion S. As described hereinabove with respect to FIG. 4D, thrombectomy device 110 may be retracted proximally to cause deployable element 126 to snare the occlusion, and/or may be rotated circumferentially to cause the fibrin strands of the occlusion to be wrapped around the deployable element. Emboli liberated during the procedure are directed proximally towards emboli removal catheter 60 due to the established retrograde flow. Increased rates of aspiration may be provided, e.g., using a syringe coupled to the proximal end of emboli removal catheter 60, to enhance the removal of emboli when the occlusion is disrupted. Advantageously, a physician selectively may actuate deployment knob 135 during the procedure to cause deployable element 126 to be transformed from a first deployment configuration to a second deployment configuration, without having to remove device 110 from the patient's vessel.

Upon disruption of the occlusion, deployment knob 135 is advanced distally to cause deployable element 126 to be returned to the contracted state, as shown in FIG. 5A. The distal end of thrombectomy device 110 then is retracted proximally into working lumen 61, and emboli removal catheter 60 may be removed from the patient's vessel.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

The invention claimed is:

1. Apparatus suitable for treating a cerebral occlusion, the apparatus comprising:
    a catheter body having proximal and distal ends and a handle affixed to the proximal end;
    an engagement section affixed to the distal end of the catheter body and consisting of a plurality of deployable elements, each deployable element having a contracted state suitable for insertion into a cerebral vessel and a deployed state, each deployable element configured to expand to a predetermined shape extending radially outward from the engagement section and in a proximal direction in the deployed state;
    comprising a micro catheter having proximal and distal ends and a lumen extending therebetween, wherein the deployable element is configured to be advanced through the lumen of the micro catheter in the contracted state;
    comprising a loading device having proximal and distal ends and a bore extending therebetween, wherein the deployable element is configured to be advanced through the bore in the contracted state; and
    an atraumatic tip affixed to a distal end of the engagement section;
    wherein each deployable element consists of a first region coupled by a bendable region to a second region, the deployable member configured so that the first region lies substantially end-to-end with the second region in the contracted state and the first and second regions are disposed adjacent to one another in the deployed state.

2. The apparatus of claim 1 wherein the deployable element comprises a shape-memory material.

3. The apparatus of claim 1 wherein the deployable element comprises en outer diameter in the deployed state that is smaller than an inner diameter of the cerebral vessel.

4. The apparatus of claim 1 wherein the engagement section comprises a tubular member having a plurality of longitudinal slits, wherein the deployable element is disposed between the longitudinal slits.

5. The apparatus of claim 1 further comprising at least one radiopaque marker disposed on the engagement section.

6. The apparatus of claim 1 wherein the proximal end of the loading device is configured to be coupled to the handle.

7. The apparatus of claim 1 wherein the deployable member is self-deploying.

8. Apparatus suitable for treating a cerebral occlusion, the apparatus comprising:
    a catheter body having proximal and distal ends and a handle affixed to the proximal end;
    an engagement section affixed to the distal end of the catheter body and deployable element, the deployable element having a contracted state suitable for insertion into a vessel and a deployed state, the deployable element configured to expand to a predetermined shape extending radially outward from the engagement section and in a proximal direction in the deployed state;
    an atraumatic tip affixed to a distal end of the engagement section;
    a micro catheter having proximal and distal ends and a lumen extending therebetween, wherein the deployable element is configured to be advanced through the lumen of the micro catheter in the contracted state; and a loading device having proximal and distal ends and a bore extending therebetween, wherein the deployable element is configured to be advanced through the bore in the contracted state.

9. The apparatus of claim 8 wherein the deployable element comprises a shape-memory material.

10. The apparatus of claim 8 wherein the deployable element comprises an outer diameter in the deployed state that is smaller than an inner diameter of a treatment vessel.

11. The apparatus of claim 8 wherein the engagement section comprises a tubular member having a plurality of longitudinal slits, wherein the deployable element is disposed between the longitudinal slits.

12. The apparatus of claim 8 further comprising at least one radiopaque marker disposed on the engagement section.

13. The apparatus of claim 8 wherein the distal end of the loading device is configured to be coupled to the proximal end of the micro catheter.

14. The apparatus of claim 8 wherein the proximal end of the loading device is configured to be coupled to the handle.

15. The apparatus of claim 8 wherein the deployable member is self-deploying.

* * * * *

UNITED STATES PATENT AND TRADEMARK OFFICE
CERTIFICATE OF CORRECTION

| | |
|---|---|
| PATENT NO. | : 7,029,488 B2 |
| APPLICATION NO. | : 10/278183 |
| DATED | : April 18, 2006 |
| INVENTOR(S) | : Schonholz et al. |

It is certified that error appears in the above-identified patent and that said Letters Patent is hereby corrected as shown below:

At column 10, lines 18 and 23: remove the word "comprising"

At column 10, line 38: change the word "en" to --an--

Signed and Sealed this

Eighth Day of August, 2006

JON W. DUDAS
*Director of the United States Patent and Trademark Office*